United States Patent [19]
Foreman et al.

[11] Patent Number: 5,976,155
[45] Date of Patent: Nov. 2, 1999

[54] SYSTEM FOR REMOVABLY SECURING A STENT ON A CATHETER ASSEMBLY AND METHOD OF USE

[75] Inventors: Philip C. Foreman, San Jose; Timothy A. Limon, Cupertino; Richard J. Saunders, Redwood City; Björn G. Svensson, Morgan Hill; Gregory W. Teaby, II, Sunnyvale, all of Calif.

[73] Assignee: Advanced Cardiovascular Systems, Inc., Santa Clara, Calif.

[21] Appl. No.: 09/263,000

[22] Filed: Mar. 5, 1999

[51] Int. Cl.⁶ .................................................. A61M 29/02
[52] U.S. Cl. ............................................ 606/108; 606/194
[58] Field of Search ..................................... 606/108, 192, 606/194, 195; 604/96, 104, 915, 97, 99, 100, 102

[56] References Cited

U.S. PATENT DOCUMENTS

| | | | |
|---|---|---|---|
| 2,701,559 | 2/1955 | Cooper | 606/192 |
| 5,102,402 | 4/1992 | Dror et al. | 604/96 |
| 5,242,394 | 9/1993 | Barath et al. | 604/96 |
| 5,372,600 | 12/1994 | Beyar et al. | 606/194 |
| 5,423,745 | 6/1995 | Todd et al. | 604/96 |
| 5,545,132 | 8/1996 | Fagan et al. | 606/194 |
| 5,626,604 | 5/1997 | Cottone, Jr. | 606/192 |
| 5,653,690 | 8/1997 | Booth et al. | 606/194 |
| 5,720,726 | 2/1998 | Marcadis et al. | 606/194 |
| 5,893,852 | 4/1999 | Morales | 606/108 |

*Primary Examiner*—Jeffrey A. Smith
*Assistant Examiner*—Eduardo C. Robert
*Attorney, Agent, or Firm*—Fulwider Patton Lee & Utecht, LLP

[57] ABSTRACT

The invention is directed to a system for removably securing a stent which generally includes an expandable member of a catheter assembly, the expandable member having outwardly extending protrusions. An expandable stent is crimped onto the expandable member such that the protrusions extend into the gaps in the stent. The stent is secured in place on the expandable member while advancing the system through tortuous body lumen passages. The stent is implanted at the desired location in the body lumen by inflating the expandable member and thereby expanding the stent into the body lumen. The protrusions are pulled away from and out of the stent gaps by deflating the expandable member and retracting the remainder of the system.

19 Claims, 3 Drawing Sheets

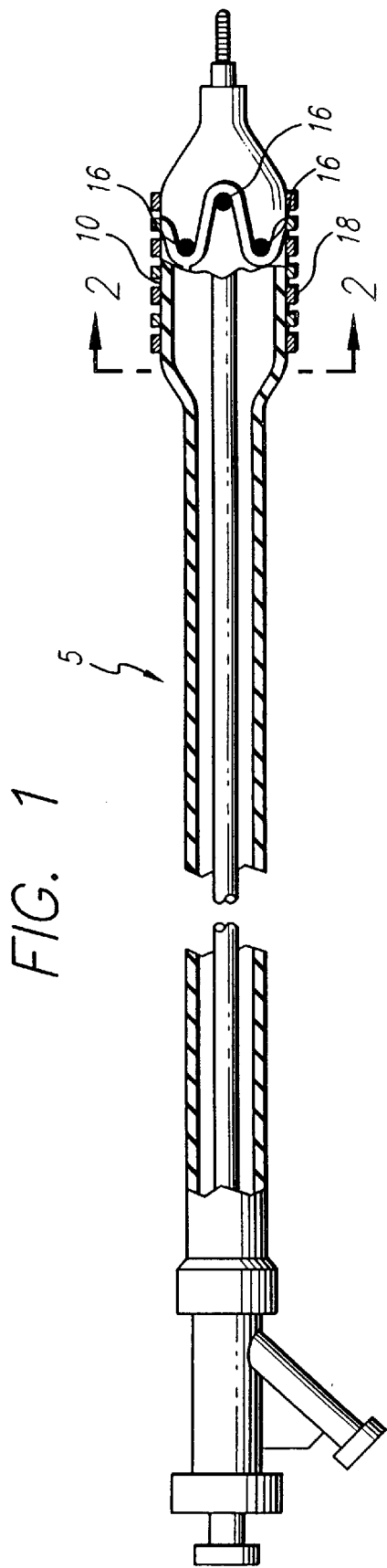
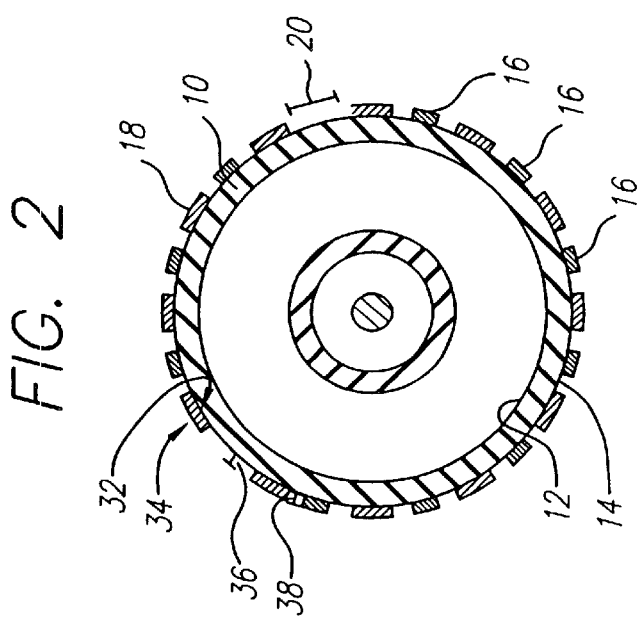

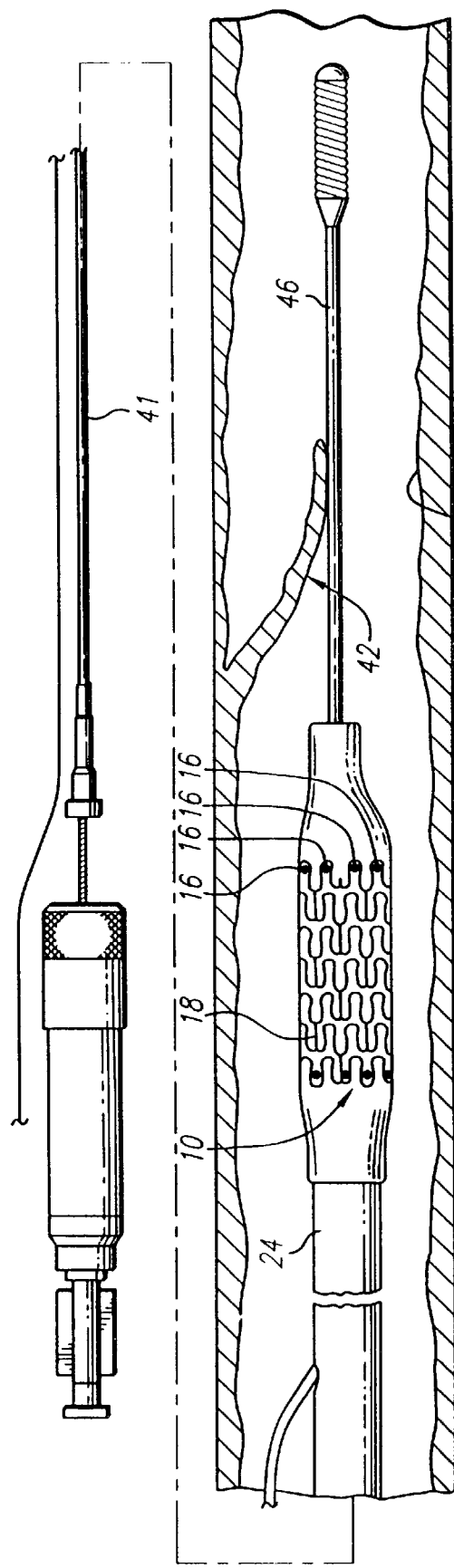
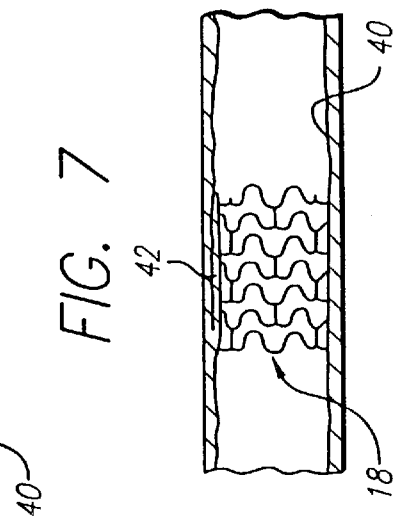
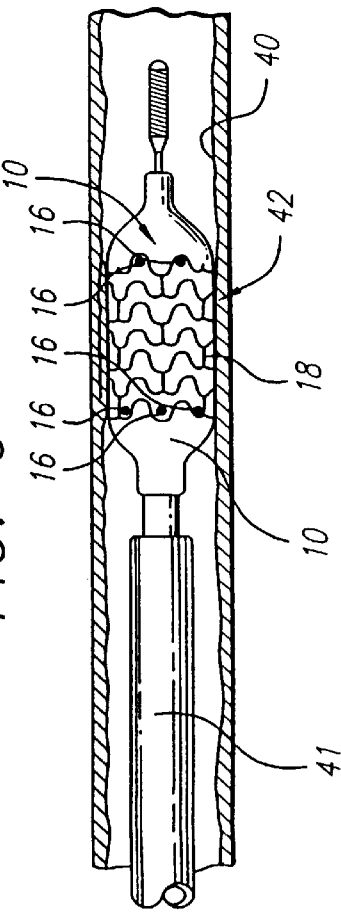
FIG. 5
FIG. 6
FIG. 7

SYSTEM FOR REMOVABLY SECURING A STENT ON A CATHETER ASSEMBLY AND METHOD OF USE

BACKGROUND OF THE INVENTION

This invention relates to devices for the treatment of heart disease and particularly to endo-arterial prosthesis, which are commonly called stents. More particularly, the invention relates to catheter assemblies for removably securing the stent to the catheter during delivery through a body lumen.

Several interventional treatment modalities are presently used for heart disease including balloon and laser angioplasty, atherectomy and by-pass surgery. In typical balloon angioplasty procedures, a guiding catheter having a performed distal tip is percutaneously introduced through the femoral artery into the cardiovascular system of a patient in a conventional Seldinger technique and advanced within the cardiovascular system until the distal tip of the guiding catheter is seated in the ostium. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon, which is made of relatively inelastic materials, is inflated to a predetermined size with radiopaque liquid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guidewires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,451,233 (Yock); and U.S. Pat. No. 5,458,651 (Klemm, et al.), which are hereby incorporated herein in their entirety by reference thereto.

One problem which can occur during balloon angioplasty procedures is the formation of intimal flaps which can collapse and occlude the artery when the balloon is deflated at the end of the angioplasty procedure. Another problem characteristic of balloon angioplasty procedures is the large number of patients which are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent development work in the treatment of heart disease has been directed to endoprosthetic devices called stents. Stents are generally cylindrically shaped intravascular devices which are placed within an artery to hold it open. The device can be used to prevent restenosis and to maintain the patency of a blood vessel immediately after intravascular treatments. In some circumstances, they can also be used as the primary treatment device where they are expanded to dilate a stenosis and then left in place.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

However, retaining the position of the stent in the proper location on the expandable member while advancing the catheter through the body lumen has been found to be difficult. If the stent is dislodged from or moved on the expandable member the system will not correctly deliver the stent into the body lumen. This would require repeating the procedure. This delays insertion of the stent into the body lumen which may adversely affect the patient's health.

Different methods have been attempted to maintain the position of the stent on the expandable member. One such method involves a protective sheath surrounding the catheter and stent assembly, which is retracted prior to inflation of the expandable member. The use of the sheath, however, increases the profile of the catheter assembly which must traverse narrow vessels. It would be an improvement to use a technique which does not increase the overall profile of the catheter assembly.

Another method has been to remove the friction reducing coating on the expandable member in the location of the stent thereby allowing the catheter assembly's pre-coated surface to hold the stent in frictional contact. This method has not proven highly efficient in maintaining the stent in the desired location.

What has been needed and heretofore unavailable is a reliable means of maintaining a stent in a desired location on a stent delivery system without increasing the overall profile of the catheter assembly. The present invention satisfies this need.

SUMMARY OF THE INVENTION

This invention is directed to an improvement in stent delivery systems for removably securing a stent onto an expandable member of a catheter. Securing the stent is accomplished by tightly crimping the stent onto the expandable member of a catheter which is modified to include outwardly extending protrusions. Stents are typically composed of a lattice configuration and therefore contain a number of gaps throughout the stents body. By positioning the protrusions and the stent so that the protrusions extend into the gaps of the stent when crimped onto the expandable member, the protrusions prevent relative motion between the stent and expandable member until the expandable member is inflated to implant the stent.

Stent delivery systems are typically composed of a catheter assembly encompassed by an expandable member such as an inflatable dilatation balloon. The stent is located about the expandable member so that the two can be expanded together. The improvement of this invention includes modifying the expandable member to include a number of protrusions. When the stent is then climped onto the modified expandable member the stent is retained in position on the expandable member while the two are in the non-expanded condition. The protrusions may also be formed after the stent has been crimped about the expandable member by coating the stent and expandable member with a fluid material which adheres to the expandable member and substantially fills the gaps in the stent.

The protrusions may be composed of an adhesive material which adheres to the expandable member or of a curable material which is cured in position after application onto the expandable member. The protrusions may also be formed integrally with the expandable member when it is manufactured.

Since a variety of stent designs are available there are a variety of protrusion patterns which may be used. The protrusions may form one or more radial patterns about the expandable member, they may also form one or more linear patterns parallel to the expandable member's longitudinal axis. The protrusions may also form a combination of these patterns, which correspond with the pattern of the gaps in the stent. The protrusions also may randomly fill gaps in the stent lattice.

The protrusions may also extend outwardly from the expandable member a variety of distances. Preferably the protrusions are formed so that their height is equal to or slightly less than the thickness of the stent. This will ensure the maximum retention strength of the protrusions without causing the protrusions to add to the overall profile and will reduce the likelihood of the catheter snagging while being inserted into the body lumen.

The invention can be used with the known configurations of stent delivery systems including, for example, over-the-wire (OTW) intravascular catheters and rapid exchange (Rx) intravascular catheters.

The invention results in a simplified method of inserting the stent into the body lumen. The catheter assembly of the invention is inserted into the body lumen without further steps being taken to prevent the dislocation of the stent. The expandable member is inflated at the desired location expanding the stent into contact with the lumen. When the expandable member is then deflated, the stent is released and the remainder of the catheter assembly may be withdrawn leaving the stent implanted within the body lumen.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is a partial cross-sectional view depicting the stent delivery system incorporating the invention.

FIG. 2 is a transverse cross-sectional view taken along lines 2—2 in FIG.

FIG. 5 is a longitudinal plan view of a rapid exchange (Rx) catheter depicting elements of the invention and inserted into a body lumen.

FIG. 6 is a longitudinal plan view of a stent delivery system having elements of the invention and depicting the expandable member being inflated and the stent implanted.

FIG. 7 is a longitudinal plan view depicting the stent implanted in the body lumen and the stent delivery system removed.

DETAILED DESCRIPTION OF PREFERRED EMBODIMENTS

Figure 3:
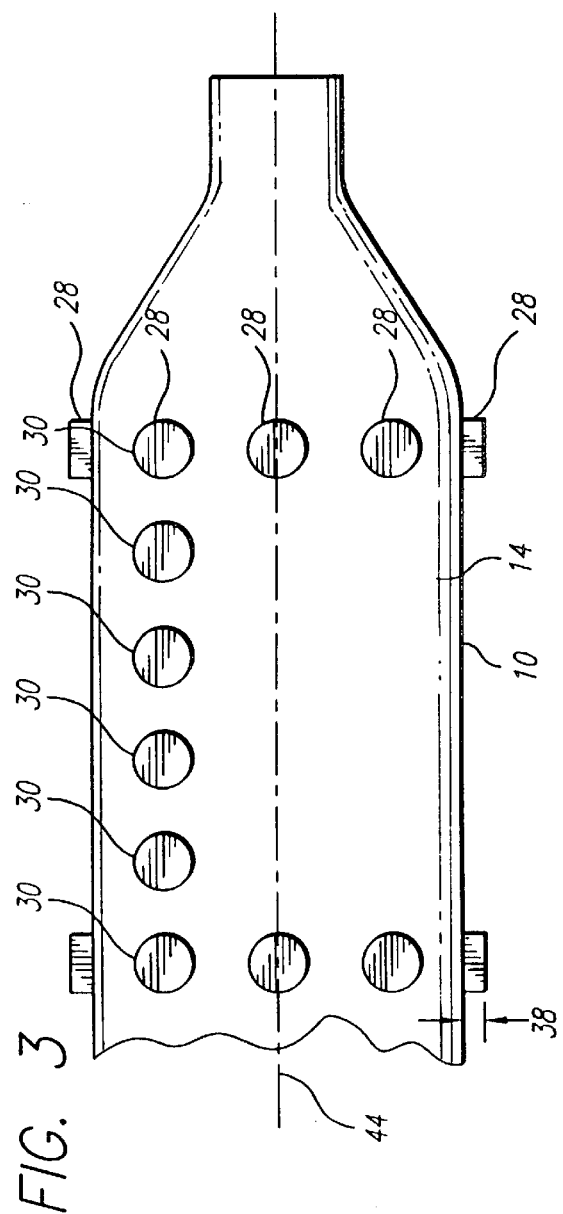
FIG. 3 is an enlarged plan view of an expandable member depicting the protrusions of the invention.

Stent delivery systems are typically comprised of catheter assemblys having expandable members attached to the distal end. The expandable member is in fluid communication with an inflation lumen in the catheter assembly so that an inflation fluid can be introduced to inflate the expandable member. Crimping an expandable stent about the expandable member allows them to be expanded together. The present invention provides protrusions on the expandable member which extend into the gaps of the crimped stent preventing relative motion between the stent and the expandable member.

FIGS. 1 and 2 illustrate catheter assembly 5 which removably secures a stent and embodies the features of the invention. Generally, the catheter assembly includes expandable member 10 having protrusions 16 extending outwardly therefrom, and attached to outer surface 14 of the expandable member. An expandable stent 18 is positioned around the expandable member 10. Preferably the stent is comprised of a lattice configuration which defines gaps 20 in the stent. The expandable stent 18 is tightly crimped about expandable member 10 such that at least some of protrusions 16 extend into gaps 20. This configuration secures the stent as the protrusions attached to the expandable member prevent the relative motion between the stent and the expandable member.

This catheter assembly with secured expandable stent 18 can be configured with known stent delivery systems. On many of these catheter systems expandable member 10 is similar to an inflatable dilatation balloon. FIGS. 1 and 2 show catheter assembly 5 as including an over-the-wire (OTW) intravascular catheter which is known in the art.

FIG. 3 illustrates several configurations for protrusions 16. The protrusions may be configured as one or more circumferential patterns 28. In this configuration, a series of protrusions are positioned on outer surface 14 of expandable member 10 about longitudinal axis 44, so that the protrusions extend along the plane that is normal to the longitudinal axis. The protrusions may also be configured as one or more axially parallel linear patterns 30. In this configuration a series of protrusions are positioned on the expandable member along its longitudinal axis 44 at the same longitudinal plane through the axis. As shown most clearly in FIG. 2, preferably height 38 of the protrusions is substantially equal to thickness 36 of expandable stent 18. The thickness 36 of the stent is defined as the distance between inner surface 32 and outer surface 34 of the stent.

Figure 4:
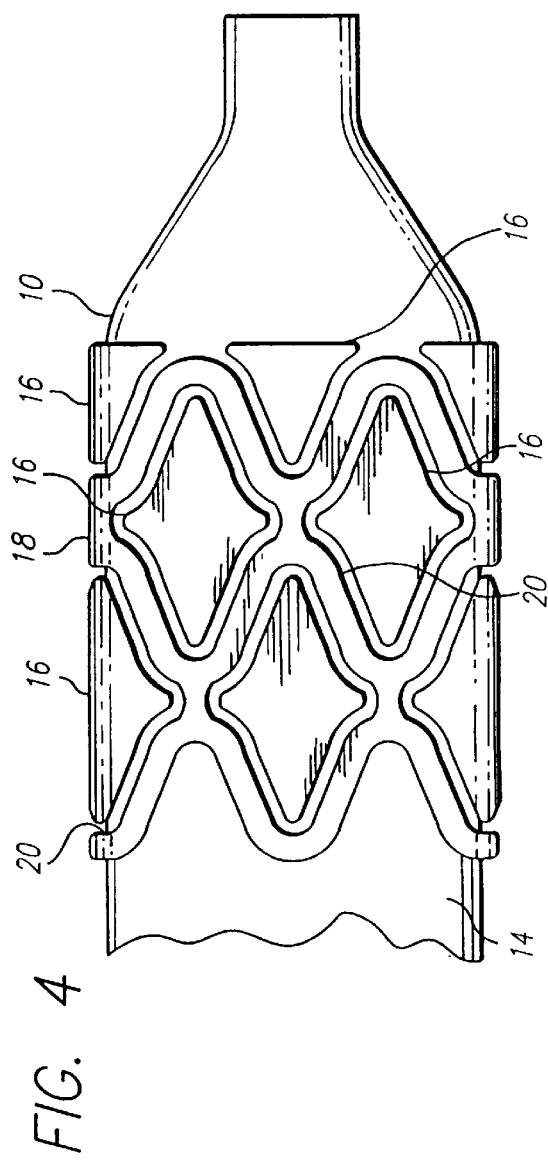
FIG. 4 is an enlarged plan view of an expandable member and expandable stent depicting protrusions of the invention.

FIG. 4 illustrates another preferred embodiment for the configuration of the protrusions. In this configuration, protrusions 16 preferably substantially match shape 26 of gaps 20 in expandable stent 18. Also, height 38 of protrusions 16 is substantially equal to thickness 36 of the expandable stent 18, so that the surface of the assembly is relatively smooth in the location of the stent and protrusions. In this configuration, not only does the invention prevent relative motion of the stent, it also reduces the tendency of the stent to snag which enhances the process of inserting the assembly and decreases risk that a portion of the stent will snag on a calcified lesion or in a tortuous vessel.

The protrusions 16 maybe formed by applying dots of adhesive material, such as polyethylene (PE) or polyethylene teraphthalate (PET), in the appropriate locations on outer surface 14 of expandable member 10. This may be accomplished by brushing the adhesive dots onto the expandable member, or applying the dots with a machine designed for precise placement to fill gaps 20. Another alternative is to form a thin-walled tubular member having integral protrusions, position the tubular member around the expandable member and heat shrink the tubular member onto the expandable member. The protrusions 16 may also be formed integrally with expandable member 10 when it is manufactured. The protrusions may be formed integrally with the expandable member by, for example, having indentations in the mold used to form the expandable member. To ensure the indentations are properly formed, elevated pressures and vacuums may be applied at appropriate locations during the molding process. The protrusions 16 may also be formed by applying dots of curable material on the outer surface 14 of the expandable member 10. An example of a curable material is the anaerobic polymer commercially available as LOCTITE 33-11 from the Loctite Corp. This material is cured by exposure to ultraviolet light. Depending on the material used, different curing methods are available. These methods include application of heat or time and are known to those in the art. The material is then cured into the desired shape and position onto the expandable member. In all these embodiments the assembly is completed by crimping stent 18 onto expandable member 10 so that protrusions 16 extend into gaps 20 of the stent and prevent relative motion between the stent and expandable member.

In another embodiment of the invention, protrusions 16 are formed after crimping expandable stent 18 onto expandable member 10. After tightly crimping the stent onto the expandable members, protrusions 16 are added to the assembly of expandable member 10 and expandable stent 10 by coating the assembly with a fluid material which substantially fills gaps 20 in the stent. This fluid material is either adhesive or curable. If the material is adhesive it is applied such that it adheres to outer surface 14 of the expandable member. If the material is curable, then it is cured in place after application. This method of forming protrusions is preferred since the assembly has a relatively smooth surface due to protrusions 16 substantially filling gaps 20 of expandable stent 18.

In another preferred method of use, the catheter assembly having a removably secured expandable stent 18 is used for delivering and implanting the stent into a body lumen when used in combination with a stent delivery system. These systems include over-the-wire (OTW) catheters (FIG. 1) and rapid exchange (Rx) catheters (FIGS. 5–7). FIGS. 5 through 7 illustrate an exemplary use of the invention using an Rx catheter. The catheter assembly with expandable stent 18 held firmly in place on expandable member 10 is inserted into body lumen 40 using stent delivery system 41. The figures illustrate a typical situation in which the invention is used after an intravascular procedure has caused dissection 42 in the arterial lining to such an extent that the lining needs support to prevent it from collapsing into the arterial passage way and obstructing flow through the vessel. In these situations, as others, the invention allows the stent to be delivered to target location 42 without further means to retain the stent on the expandable member.

Preferably, stent delivery system 41 is advanced over guide wire 46 which is already in position distal to target location 42. Since the stent is removably attached to the expandable member during delivery through the patient's vasculature, it will not move relative to the expandable member until it is positioned at the target location. Protrusions 16 retain the stent until it is desired to expand and implant the stent. As illustrated in FIG. 6, expandable member 10 is inflated thereby expanding and implanting expandable stent 18 into body lumen 40. This may be accomplished, for example, by introducing radiopaque fluid into the interior of the expandable member under substantial pressure as is known in the art. The expandable member is then deflated and the expandable stent remains expanded and in place in the target location of the body lumen. With the expandable stent in the expanded condition and the expandable member in the deflated condition, protrusions 16, being attached to the surface 14 of the expandable member, no longer extend into gaps 20 of the expandable stent. While the expandable stent remains implanted in the target location of the body lumen, the catheter assembly is removed from the body lumen.

The dimensions of the intravascular catheter will generally follow the dimensions of intravascular catheters used in angioplasty procedures in the same arterial location. Typically, the length of a catheter for use in the coronary arteries is about 150 cm, the outer diameter of the catheter shaft is about 0.035 inch (0.89 mm), the length of the balloon is typically about 2 cm and the inflated diameter about 1 to about 8 mm.

The materials of construction of the catheter and expandable member may be selected from those used in conventional balloon angioplasty catheters, such as those described in the patents incorporated by reference.

While the present invention has been described herein in terms of delivering an expandable stent to a desired location within a patient's body lumen, the delivery system can also be employed to deliver stents to locations within other body lumens so that the stents can be expanded to maintain the patency of those body lumens. Various changes and improvements may also be made to the invention without departing from the scope thereof.

What is claimed is:

1. A catheter assembly removably securing an expandable stent for delivering and implanting within a body lumen, comprising:

an expandable member disposed at a distal section of a catheter, the expandable member configured as an elongated cylinder defining an inner surface and an outer surface; and at least one protrusion disposed on the outer surface of the expandable member and extending radially outwardly therefrom;

whereby an expandable stent is tightly crimped onto the outer surface of the expandable member and the at least one protrusion.

2. The catheter assembly of claim 1, wherein the expandable stent comprises a lattice configuration defining gaps in the expandable stent, the expandable stent being tightly crimped about the outer surface of the expandable member so that the at least one protrusion extends into the gaps in the expandable stent.

3. The catheter assembly of claim 2, wherein a plurality of protrusions are configured in at least one radial pattern about the outer surface of the expandable member corresponding to the gaps in the stent.

4. The catheter assembly of claim 2, wherein a plurality of protrusions are configured in at least one axially parallel linear pattern along the outer surface of the expandable member corresponding to the gaps in the stent.

5. The catheter assembly of claim 2, wherein the expandable stent has an inner surface and an outer surface defining a thickness therebetween, and the at least one protrusion extends outwardly from the outer surface of the expandable member a distance substantially equal to the thickness of the stent.

6. The catheter assembly of claim 2, wherein the gaps in the stent form predetermined shapes and the at least one protrusion being configured to fill the shapes so that the catheter assembly has a relatively smooth surface at the location of the stent and the at least one protrusion.

7. The catheter assembly of claim 1, wherein the expandable member is an inflatable balloon.

8. The catheter assembly of claim 1, wherein the catheter is configured as an over-the-wire intravascular catheter.

9. The catheter assembly of claim 1, wherein the catheter is configured as a rapid exchange intravascular catheter.

10. The catheter assembly of claim 1, wherein the catheter is configured as a monorail catheter.

11. The assembly of claim 1, wherein the at least one protrusion is formed from an adhesive material.

12. The assembly of claim 1, wherein the at least one protrusion is formed from a curable material.

13. The assembly of claim 1, wherein the at least one protrusion is integral with the expandable member.

14. A method of removably securing an expandable stent mounted on a catheter assembly, comprising:

providing an expandable member disposed at a distal section of a catheter, the expandable member configured as an elongated cylinder defining an inner surface and an outer surface;

providing an expandable stent having a lattice configuration defining gaps within the stent;

aligning the stent about the expandable member;

adhering a material to the outer surface of the expandable member so that the material forms at least one protrusion extending radially outwardly from the outer surface of the expandable member; and crimping the expandable stent onto the outer surface of the expandable member such that the at least one protrusion extends into the gap(s) in the expandable stent;

whereby the expandable stent is removably secured on the expandable member.

15. The method of claim 14, wherein adhering the material to the outer surface of the expandable member further comprises:

providing a cylinder of elastomeric material having at least one integral protrusion extending radially outward;

disposing the cylinder about the outer surface of the expandable member; and heat-shrinking the cylinder onto the expandable member.

16. The method of claim 14, wherein the material is cured after application onto the outer surface of the expandable member.

17. A method of removably securing an expandable stent on a catheter assembly, comprising:

providing an expandable member at a distal section of a catheter and having an inner surface and an outer surface with a plurality of integral protrusions extending outwardly from the outer surface of the expandable member;

providing an expandable stent having a lattice configuration defining gaps in the stent;

aligning the stent about the expandable member; and tightly crimping the expandable stent onto the outer surface of the expandable member such that at least some of the protrusions extend into at least some of the gaps in the expandable member thereby removably retaining the expandable stent on the expandable member.

18. A method of removably securing an expandable stent on a catheter assembly, comprising:

providing an expandable member shaped as an elongated cylinder defining an inner surface and an outer surface;

providing an expandable stent having a lattice configuration defining gaps in the stent;

crimping the stent onto the expandable member; and coating the expandable member and stent with an adhesive such that the material substantially fills the gaps in the stent and the material adheres to the outer surface of the expandable member thereby forming protrusions on the expandable member;

whereby the expandable stent is removably secured on the expandable member.

19. A method of delivering and implanting expandable stent at a desired location within a body lumen, the method comprising:

providing a catheter assembly having an expandable member shaped as an elongated cylinder defining an inner surface and an outer surface and having a plurality of protrusions extending radially outwardly from the outer surface;

providing an expandable stent having a lattice configuration defining gaps in the stent;

crimping the stent onto the expandable member so that the protrusions extend into the gaps in the expandable stent;

advancing the catheter assembly through the body lumen to the desired location;

inflating the expandable member thereby expanding and implanting the expandable stent at the desired location;

deflating the expandable member so that the protrusions no longer extend into the gaps in the stent; and withdrawing the catheter assembly from the body lumen.

\* \* \* \* \*

UNITED STATES PATENT AND TRADEMARK OFFICE
CERTIFICATE OF CORRECTION

PATENT NO. : 5,976,155
DATED : Nov. 2, 1999
INVENTOR(S) : Philip C. Foreman, Timothy A Limon, Richard J Saunders, Bijorn G. Svensson, Gregory W. Teaby, II It is certified that error appears in the above-identified patent and that said Letters Patent is hereby corrected as shown below:

Title page, under "U.S. PATENT DOCUMENTS", add the following:
```
--4,733,665    3/1988     Palmaz
  5,108,416    4/1992     Ryan, et al.
  5,158,548   10/1992     Lau, et al.
  5,242,399    9/1993     Lau, et al.
  5,344,426    9/1994     Lau, et al.
  5,455,646    8/1995     Euteneuer, et al.
  5,514,154    3/1996     Lau, et al.
  5,571,135   11/1996     Fraser, et al.
  5,836,965   11/1998     Jendersee, et al.--
```

Signed and Sealed this

Third Day of April, 2001

Attest:

NICHOLAS P. GODICI

*Attesting Officer*    Acting Director of the United States Patent and Trademark Office